July 21, 1959 H. ROBINSON Plant Pat. 1,853
ROSE PLANT
Filed Nov. 25, 1958
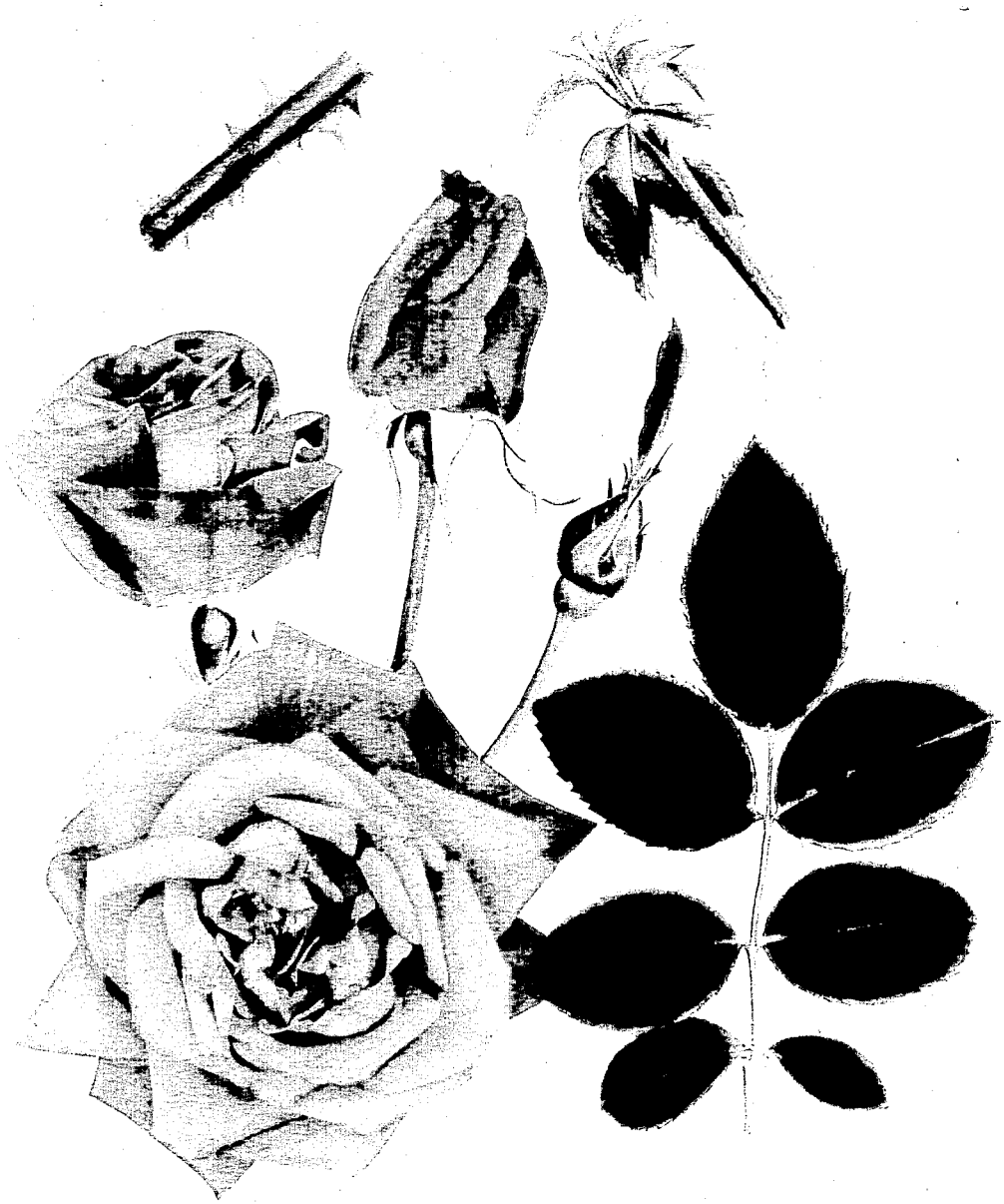
Inventor.
Herbert Robinson
By: Robb & Robb
Attorneys.

United States Patent Office

Plant Pat. 1,853
Patented July 21, 1959

1,853

ROSE PLANT

Herbert Robinson, Burbage, Hinckley, England, assignor to Jackson & Perkins Company, Newark, N.Y., a corporation of New York Application November 25, 1958, Serial No. 776,249

1 Claim. (Cl. 47—61)

The present invention relates to a new and distinct variety of rose plant of the hybrid tea class, which was originated by me by crossing the hybrid tea variety "F. W. Alesworth" (unpatented) with the hybrid tea variety "Charles Mallerin" (U.S. Plant Patent No. 933).

The primary objective of this breeding was to produce a new rose variety which bears dark red flowers similar to those of the variety "Charles Mallerin," but which is endowed with better plant and better flower production characteristics. This objective was fully achieved, along with other desirable improvements, as evidenced by the following unique combination of characteristics which are outstanding in the new variety and which distinguish it from its parents as well as from all other varieties of which I am aware:

(1) Strong stems of upright habit;
(2) Irregular and corrugated foliage;
(3) Good flower production;
(4) A Scarlet Red general color tonality of the flowers which persists and does not appreciably change during the life of the bloom; and
(5) A strong Old Rose perfume fragrance which is especially desirable in a red rose.

Asexual reproduction of the new variety by budding, as performed at Newark, New York, U.S.A. and also at Pleasanton, California, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"F. W. Alesworth."
*Pollen parent.*—"Charles Mallerin."
Classification:
*Botanic.*—Hybrid tea.
*Commercial.*—Hybrid tea.

*Flower*

(Observations made from specimens grown outdoors at Newark, New York, U.S.A. in mid-afternoon in the early part of September.)

Blooming habit: Recurrent—continuous.
Bud:
*Size.*—Large.
*Form.*—Ovoid; is not affected by wet or hot weather.
*Color.*—When sepals first divide—Oxblood Red, Plate 1. When petals begin to unfurl—Carmine, Plate 1. When half-blown: inside of petals—Carmine, Plate 1, with outer edges of petals lightly overcast with Spectrum Red, Plate 1; reverse of petals—Spectrum Red, Plate 1.
*Sepals.*—Branched, with "hood" above bud; curl back when petals begin to unfurl. Color: inside—Pale Fluorite Green, Plate 32; outside—Biscay Green, Plate 17.
*Calyx.*—Color—Biscay Green, Plate 17. Shape—apple. Size—small. Aspect—smooth. Odor when rubbed—none.
*Peduncle.*—Length — medium. Aspect — rough. Strength — erect; heavy. Color — Light Bice Green, Plate 17.
*Opening.*—Opens up well; is not affected by adverse weather conditions.
Bloom:
*Size.*—Large. Average size when fully expanded—5½ inches.
*Borne.*—Singly.
*Stems.*—Medium length; strong.
*Form (when first open).*—Cupped. Permanence—retains its form to the end.
*Petalage.*—Double (full but open center). Number of petals under normal conditions—30.
*Color.*—Center of flower—Scarlet Red, Plate 1. Outer petals—Carmine, Plate 1, lightly overcast with Spectrum Red, Plate 1. Base of petals (aiglet)—Pinard Yellow, Plate 4. Inside of petals—Carmine, Plate 1, lightly overcast with Scarlet Red, Plate 1. Reverse of petals—Spectrum Red, Plate 1, lightly overcast with Eugenia Red, Plate 13. General tonality from a distance—Scarlet Red, Plate 1.
*Discoloration.*—General tonality at end of first day—Scarlet Red, Plate 1. Second day—Carmine, Plate 1, lightly overcast with Spectrum Red, Plate 1. Third day—Carmine, Plate 1, lightly overcast with Scarlet Red, Plate 1.
Petals:
*Texture.*—Leathery; is not affected by wet or hot weather.
*Appearance.*—Inside—velvety. Outside—satiny.
*Form.*—Round.
*Arrangement.* — Imbricated (regularly arranged shingle-like).
*Petaloids in center.*—Few; large.
*Persistence.*—Drop off cleanly.
*Fragrance.*—Strong. Nature—"Old Rose perfume" (centifolia).
*Lasting quality.*—On the plant—long. As cut flower—long.

*Genital organs*

Stamens, anthers: Medium size; many; regularly arranged around styles. Color — Capucine Yellow, Plate 3.
Stamens, filaments (threads): Long. Color—Eugenia Red, Plate 13.
Pollen: Color—Pale Pinkish Cinnamon, Plate 29.
Styles: Columnar; uneven length; medium length; thin.
Stigmas: Color—Maize Yellow, Plate 4.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Normal.
*Color.*—New foliage: upper side — Rinnemann's Green, Plate 18; under side—Courge Green, Plate 17, lightly overcast with Eugenia Red, Plate 13. Old foliage: upper side—Elm Green, Plate 17; under side—Light Elm Green, Plate 17.

*Shape.*—Oval.

*Texture.*—Upper side—leathery; irregular and corrugated. Under side—smooth.

*Ribs and veins.*—Ordinary.

*Edge.*—Serrated (saw-toothed).

*Serration.*—Both double and single; small.

*Leaf stem.*—Color—Biscay Green, Plate 17. Under side—smooth.

*Stipules.*—Medium length; smooth.

Wood:

*New wood.*—Color—Parrot Green, Plate 6. Bark—smooth.

*Old wood.*—Color—Cress Green, Plate 31. Bark—smooth.

Thorns:

*Thorns.*—Quantity: on main stalks from base—ordinary; on laterals from stalk — ordinary.

Form—narrow base; medium length; some hooked downward and some hooked upward. Color (when young)—Eugenia Red, Plate 13. Position—irregular.

*Prickles.*—Quantity: on main stalks from base—none; on laterals from stalk—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of strong stems of upright habit, irregular and corrugated foliage, good flower production, a Scarlet Red general color tonality of the flowers which persists and does not appreciably change during the life of the bloom, and a strong "Old Rose perfume" fragrance of the flowers.

No references cited.